United States Patent
Davies et al.

(10) Patent No.: US 6,924,338 B1
(45) Date of Patent: Aug. 2, 2005

(54) ZWITTERIONIC POLYMER BLEND MATERIALS

(75) Inventors: Martyn Christopher Davies, Nottingham (GB); Stuart Clarke, Nottinghamshire (GB); Andrew Lennard Lewis, Surrey (GB)

(73) Assignee: Biocompatibles UK Limited, Farnham (GB)

( * ) Notice: Subject to any disclaimer, the term of this patent is extended or adjusted under 35 U.S.C. 154(b) by 271 days.

(21) Appl. No.: 10/110,546

(22) PCT Filed: Oct. 16, 2000

(86) PCT No.: PCT/GB00/03985

§ 371 (c)(1),
(2), (4) Date: Apr. 15, 2002

(87) PCT Pub. No.: WO01/27209

PCT Pub. Date: Apr. 19, 2001

(30) Foreign Application Priority Data

Oct. 15, 1999 (GB) ............................................. 9924502

(51) Int. Cl.$^7$ .......................... C08L 27/10; C08L 33/04; C08L 39/04; C08L 43/00; C08L 45/00
(52) U.S. Cl. ...................... 525/203; 525/209; 525/210; 525/211; 525/222; 525/223
(58) Field of Search ................................ 525/203, 209, 525/210, 211, 222, 223

(56) References Cited

U.S. PATENT DOCUMENTS 5,712,326 A * 1/1998 Jones et al. ................. 523/105

FOREIGN PATENT DOCUMENTS

| EP | 0 079 197 A2 | 5/1983 |
|---|---|---|
| EP | 0 823 458 A1 | 2/1998 |
| WO | WO 87/02684 | 5/1987 |
| WO | WO 94/14897 | 7/1994 |

OTHER PUBLICATIONS

Hayward et al., "Biomembrane surfaces as models for polymer design: the potential for haemocompatibility," *Biomaterials*, (May 1984), vol. 5, pp. 135–142.

* cited by examiner

*Primary Examiner*—Nathan M. Nutter
(74) *Attorney, Agent, or Firm*—Sughrue Mion (57) ABSTRACT

A polymer blend for use in a biomedical application comprising: (A) a polymer A, bearing zwitterionic pendant groups; and (B) a hydrophobic addition polymer B, selected from the group consisting silyl(alk)acrylates, alkyl(alk)acrylamides, dialkyl(alk)acrylamides, and alkyl(alk)acrylate polymers, wherein the structure of the blend exhibits phase separation forming a micro-phase segregated structure at a surface. Articles, methods of production and liquid blend compositions are also disclosed. Preferably A is a copolymer of 15 to 30 mole % 2-methacryloyloxyethyl-2-trimethylammonium ethyl phosphate inner salt and 85 to 70 mole % of a $C_{6-18}$ alkyl methacrylate, and B is a homopolymer of a $C_{4-18}$ alkyl(meth)acrylate, blended in weight proportions of 1:1 to 1:50.

13 Claims, 5 Drawing Sheets

Figure 6c

ZWITTERIONIC POLYMER BLEND MATERIALS

The present invention relates to a new polymeric materials, especially suitable for use in biomedical applications, processes for their production, articles formed from such materials and processes for modifying the physical and biological properties of plastic materials.

The medical device industry frequently employs a range of thermoplastic, elastomeric and thermoset materials in medical devices. Many of these polymers were originally developed as engineering materials and their physical and mechanical properties reflect this. Thus a plastic may be employed as a medical device because it possesses physical and mechanical properties suitable for use in a biological environment. However, until recently little attention was paid to the biological properties of these materials. This has resulted in a number of problems with current device materials as a result of adverse biological reactions. Silicone rubbers have been shown to leach toxic silicones when implanted, polyurethanes have been found to degrade by macrophage attack and natural rubbers have caused severe allergic reactions. In addition, PVC, a widely used polymer for medical devices, often contains large quantities of the plasticiser bis-(2-ethylhexyl)phthalate and many studies now shown this to be toxic. It is clear, therefore, that many materials possess properties which render them unsuitable for use in biological applications.

Previous attempts to prepare biocompatible materials have mimicked the surface of red blood cells which under normal circumstances exist in the blood without causing any adverse reactions. These cell membranes comprise a phospholipid bilayer with the phosphorylcholine group dominating the external membrane surface. It is believed this outer surface avoids adverse reaction with other biological components. Lipids containing phosphorylcholine groups have been coated on to the surface of device materials and bloodclotting studies showed that they rendered the surface more biocompatible (J A Hayward & D Chapman, Biomaterials, Vol. 5, 135, 1984). These phospholipids have also been used as plasticisers in commercial polymers and have again improved the biocompatibility of the base material (WO-A-87/02684). However these two approaches nevertheless possess disadvantages.

Coating the surface of a finished device has a number of problems, one being the difficulty in coating devices with complex shapes or multiple components; in practice a multi-component device can be impossible to coat. In addition the degree of biocompatibility is dependent on the quality of the coating and how strongly it is bound to the surface; thus defects or scratches in the coating will reduce its effectiveness. The use of a lipid as a plasticiser goes some way to overcome these problems, but the lipid is free to move through the material and can eventually leach out of the system. This can again lead to a reduction in the level of biocompatibility. The lipid also has in addition no mechanical strength and can therefore only be used to soften the base polymer.

In certain circumstances it is desirable to provide a coating in which defined areas provide good biocompatibility whilst other areas invoke an interaction with protein. This has application in devices, graft or other surfaces which require partial assimilation with biological tissue or environments.

We have now devised new blended polymeric materials which seek to overcome these disadvantages. The blends combine the desirable physical and/or mechanical properties of an engineering polymer with the biocompatible properties of a polymer bearing pendant zwitterionic, for example phosphoryl choline, groups.

In our earlier application number WO-A-94/14897 we describe blends of zwitterionic polymers with polymers having desirable physical or mechanical properties. The polymers with which the zwitterionic polymers were blended included polymethylmethacrylate, polyethylene, polystyrene and polyacrilonitrile/polyvinylchloride. Blending processes included forming a common solution of the two polymers in a suitable solvent or solvent mixture. The zwitterionic polymers were usually copolymers of 2-methacryloyloxyethyl-2'-trimethylammonium ethyl phosphate inner salt (MPC) with comonomers, including a variety of hydrophobic monomers, for instance $C_{4-18}$-alkyl methacrylate, and fluoroalkyl methacrylates. The molar proportion of zwitterionic monomer in the polymer was in the range 1:(0.5 to 4). In EP-A-0823458, copolymers of MPC with hydrophobic comonomer are blended with hydrophobic polymers, usually a segmented polyurethane. The hydrophobic comonomer was selected from styrene and its derivatives, alkyl(meth)acrylates such as linear or branched alkyl methacrylates, vinyl ethers, vinyl chloride, alk-1-ene, alycyclic methacrylates and arylurethane alkyl methacrylates. The zwitterionic monomer may be present in the copolymer in a molar proportion in the range 10 to 70%. All the worked examples used around 30%.

The solid blends are said to show phase separation comprising domains of several hundred $\mu$m or less consisting of the zwitterionic copolymer distributed in continuous hydrophobic polymer. In the examples the main sizes are in the range 1 to 45 $\mu$m, as judged under SEM, after exposing the film surface to osmium tetroxide followed by sputtering with carbon.

In EP-A-0079197, polymers with zwitterionic groups which are sulpho- or carboxybetaines are used as antistatic agents or hygroscopic agents in thermoplastic films and fibres for instance for making clothing.

The present invention accordingly provides the use in a biomedical application of a solid blend of:

(A) a polymer A, bearing zwitterionic pendant groups formed from a mixture of ethylenically unsaturated monomers including i) 5 to 70 mol % zwitterionic monomer of the general formula I:

$$YBX \qquad \qquad I$$

wherein

B is a straight or branched alkylene (alkanediyl), alkyleneoxaalkylene or alkylene oligo-oxaalkylene chain optionally containing one or more fluorine atoms up to and including perfluorinated chains or, if X or Y contains a terminal carbon atom bonded to B, a valence bond;

X is a zwitterionic group; and

Y is an ethylenically unsaturated polymerisable group selected from $CH_2=C(R)—CH_2—O—$, $CH_2=C(R)—CH_2OC(O)—$, $CH_2=C(R)OC(O)—$, $CH_2=C(R)—O—$, $CH_2=C(R)CH_2OC(O)N(R^1)—$, $R^2(OOCCR=CRC(O)—O—$, $RCH=CHC(O)O—$, $RCH=C(COOR^2)CH_2—C(O)—O—$, wherein:

R is hydrogen or a $C_1$-$C_4$ alkyl group;

$R^1$ is hydrogen or a $C_1$-$C_4$ alkyl group or $R^1$ is —B—X where B and X are as defined above; and $R^2$ is hydrogen or a $C_{1-4}$ alkyl group;

A is —O— or —NR$^1$—;

K is a group —$(CH_2)_pOC(O)$—, —$(CH_2)_pC(O)O$—, —$(CH_2)_pOC(O)O$—, —$(CH_2)_pNR^3$—, —$(CH_2)_pNR^3C(O)$—, —$(CH_2)_pC(O)NR^3$—, —$(CH_2)_pNR^3C(O)O$—, —$(CH_2)_pOC(O)NR^3$—, —$(CH_2)_pNR^3C(O)NR^3$— (in which the groups $R^3$ are the same or different), —$(CH_2)_pO$—, —$(CH_2)_pSO_3$—, or, optionally in combination with B, a valence bond p is from 1 to 12; and $R^3$ is hydrogen or a $C_1$-$C_4$ alkyl group; and ii) 50 to 90 mol % of a comonomer having the general formula II $$Y^1R^4 \qquad \qquad II$$

wherein $Y^1$ is selected from $CH_2=C(R^5)—CH_2—O—$, $CH_2=C(R^5)—CH_2OC(O)—$, $CH_2=C(R^5)OC(O)—$, $CH_2=C(R^5)—O—$, $CH_2=C(R^5)CH_2OC(O)N(R^6)—$, $R^7OOCCR^5=CR^5C(O)—O—$, $R^5CH=CHC(O)O—$, $R^5CH=C(COOR^7)CH_2—C(O)—O—$, wherein:

$R^5$ is hydrogen or a $C_1$-$C_4$ alkyl group;

$R^6$ is hydrogen or a $C_1$-$C_4$ alkyl group or $R^6$ is $R^4$;

$R^7$ is hydrogen or a $C_{1-4}$ alkyl group;

$A^1$ is —O— or —NR$^6$—; and $K^1$ is a group —$(CH_2)_qOC(O)$—, —$(CH_2)_qC(O)O$—, —$(CH_2)_qOC(O)O$—, —$(CH_2)_qNR^8$—, —$(CH_2)_qNR^8C(O)$—, —$(CH_2)_qC(O)NR^8$—, —$(CH_2)_qNR^8C(O)O$—, —$(CH_2)_qOC(O)NR^8$—, —$(CH_2)_qNR^8C(O)NR^8$— (in which the groups $R^8$ are the same or different), —$(CH_2)_qO$—, —$(CH_2)_qSO_3$—, or a valence bond q is from 1 to 12;

and $R^8$ is hydrogen or a $C_1$-$C_4$ alkyl group;

and $R^4$ is a straight, branched or cyclic $C_{6-24}$ alkyl, alkoxyalkyl having a total of 6 to 24 carbon atoms or oligoalkoxyalkyl chain $C_pH_{2p+1}(OC_qH_{2q})_s$ in which p is 3–24, s is in the range 2 to 50, in the groups $C_qH_{2q}$ the q's are the same or different, each q is 2–6 provided that at least half of the q's are 3 or more when p is less than 8, $C_{1-24}$, fluoroalkyl, straight or branched $C_{6-24}$ alkenyl, $C_{6-24}$ alkynyl, $C_{6-24}$ aryl, $C_{6-24}$ aralkyl, or a siloxane group —$(CR^{18a}_2)_{qq}(SiR^{19}_2)(OSiR^{19}_2)_{pp}R^{19}$ in which each group $R^{18}$ is the same or different and is hydrogen or alkyl of 1 to 4 carbon atoms, or aralkyl, each group $R^{19}$ is alkyl of 1 to 4 carbon atoms, qq is from 1 to 6 and pp is from 0 to 49; and (B) a hydrophobic addition polymer B, selected from the group consisting of silyl(alk)acrylates, $C_{4-24}$ alkyl(alk) acrylamide, di $C_{4-18}$ alkyl(alk)acrylamides, and $C_{4-24}$alkyl(alk)acrylate polymers, wherein the structure of the blend exhibits phase separation forming a microphase segregated structure at the surface of an article.

There are also provided novel liquid blends of polymer A and polymer B, articles incorporating the solid blends, liquid blending processes and processes for producing the solid blends from the liquid blends.

(A) Polymer Bearing Zwitterionic Pendant Groups

The polymer is a copolymer of a zwitterionic monomer containing a zwitterionic group and a comonomer containing a hydrophobic group, usually an alkyl group. The presence of residues of such comonomers may serve to alter or improve the compatibility of the polymer (A) for the polymer (B) in the blend of the present invention.

Preferably, such a hydrophobic group is an alkyl or fluoroalkyl group.

In addition to the zwitterionic monomer and comonomer, such copolymers may further comprise residues of a functional comonomer containing a reactive functional group or an ionic group. Reactive groups may serve to crosslink the copolymer (A) and/or bind the copolymer (A) to the polymer (B) having desirable physical and/or mechanical properties. In addition such reactive groups may provide reactive moieties at the surface of the blend or may serve to bind the copolymer (A) to the surface of an article. Such functional comonomers are present in the monomer mixture is an amount up to 25 mol %, preferably in the range 0.1 to 10 mol %.

In addition, the monomer mixture for forming polymer (A) may further comprise residues of one or more diluent comonomers, for instance in an amount up to 45 mol %, preferably 1 to 25 mol %.

Monomers and comonomers of ethylenically unsaturated monomers which may be used in the preferred polymers (A) will now be described in more detail.

A.1. Monomers Containing a Zwitterionic Group

In the zwitterionic monomer the general formula I, the zwitterionic group preferably has the general formula III

III in which the moieties $A^2$ and $A^3$, which are the same or different, are —O—, —S—, —NH— or a valence bond, preferably —O—, and $W^+$ is a group comprising an ammonium, phosphonium or sulphonium cationic group and a group linking the anionic and cationic moieties which is preferably a $C_{1-12}$-alkanediyl group, preferably in which $W^+$ is a group of formula

W¹ is alkanediyl of 1 or more, preferably 2–6 carbon atoms optionally containing one or more ethylenically unsaturated double or triple bonds, disubstituted-aryl (arylene), alkylene arylene, arylene alkylene, or alkylene aryl alkylene, cycloalkanediyl, alkylene cycloalkyl, cycloalkyl alkylene or alkylene cycloalkyl alkylene, which group $W^1$ optionally contains one or more fluorine substituents and/or one or more functional groups; and either the groups $R^9$ are the same or different and each is hydrogen or alkyl of 1 to 4 carbon atoms, preferably methyl, or aryl, such as phenyl, or two of the groups $R^9$ together with the nitrogen atom to which they are attached form an aliphatic heterocyclic ring containing from 5 to 7 atoms, or the three groups $R^9$ together with the nitrogen atom to which they are attached form a fused ring structure containing from 5 to 7 atoms in each ring, and optionally one or more of the groups $R^9$ is substituted by a hydrophilic functional group, and the groups $R^{10}$ are the same or different and each is $R^9$ or a group $OR^9$, where $R^9$ is as defined above; or Het is an aromatic nitrogen-, phosphorus- or sulphur-, preferably nitrogen-, containing ring, for example pyridine.

Most preferably, the zwitterionic group of the formula III, has the general formula IV:

IV where the groups $R^{11}$ are the same or different and each is hydrogen or $C_{1-4}$ alkyl, and m is from 1 to 4, in which preferably the groups $R^{11}$ are the same preferably methyl.

Alternatively, the zwitterionic group may be a betaine group (ie in which the cation is closer to the backbone), for instance a sulpho-, carboxy- or phospho-betaine. A betaine group should have no overall charge and is preferably therefore a carboxy- or sulpho-betaine. If it is a phosphobetaine the phosphate terminal group must be a diester, i.e., be esterified with an alcohol. Such groups may be represented by the general formula V

V in which $A^4$ is a valence bond, —O—, —S— or —NH—, preferably —O—;

V is a carboxylate, sulphonate or phosphate diester (monovalently charged) anion;

$R^{12}$ is a valence bond (together with $A^4$) or alkanediyl, —C(O)alkylene- or —C(O)NHalkylene preferably alkanediyl, and preferably containing from 1 to 6 carbon atoms in the alkanediyl chain;

the groups $R^{13}$ are the same or different and each is hydrogen or alkyl of 1 to 4 carbon atoms or the groups $R^{13}$ together with the nitrogen to which they are attached form a heterocyclic ring of 5 to 7 atoms; and $R^{14}$ is alkyanediyl of 1 to 20, preferably 1 to 10, more preferably 1 to 6 carbon atoms.

One preferred sulphobetaine monomer has the formula VI

VI where the groups $R^{15}$ are the same or different and each is hydrogen or $C_{1-4}$ alkyl and s is from 2 to 4.

Preferably the groups $R^{15}$ are the same. It is also preferable that at least one of the groups $R^{15}$ is methyl, and more preferable that the groups $R^{15}$ are both methyl.

Preferably s is 2 or 3, more preferably 3.

Alternatively the zwitterionic group may be an amino acid moiety in which the alpha carbon atom (to which an amine group and the carboxylic acid group are attached) is joined through a linker group to the backbone of the biocompatible polymer. Such groups may be represented by the general formula VII

VII in which $A^5$ is a valence bond, —O—, —S— or —NH—, preferably —O—, $R^{16}$ is a valence bond (optionally together with $A^5$) or alkanediyl, —C(O)alkylene- or —C(O)NHalkylene, preferably alkanediyl and preferably containing from 1 to 6 carbon atoms; and the groups $R^{17}$ are the same or different and each is hydrogen or alkyl of 1 to 4 carbon atoms, preferably methyl, or two or three of the groups $R^{17}$, together with the nitrogen to which they are attached, form a heterocyclic ring of from 5 to 7 atoms, or the three group $R^{17}$ together with the nitrogen atom to which they are attached form a fused ring heterocyclic structure containing from 5 to 7 atoms in each ring.

B is preferably $C_{2-18}$, more preferably $C_{2-6}$, -alkanediyl, branched, or, preferably, straight chain, that is $(CH_2)_r$, where r is 2 to 18, preferably 2 to 6.

Most preferred definitions of $R^4$ are $C_{8-16}$-alkyl, -fluoroalkyl, -alkenyl or -alkynyl.

Functional comonomer may have the general formula VIII

VIII where $R^{20}$ is a valence bond or, more preferably, a straight or branched $C_{2-24}$ alkanediyl, alkyleneoxyalkylene having total of 2 to 24 carbon atoms or alkylene (oligooxyalkylene) group having a total of 2 to 24 carbon atoms and Q is a functional group selected from cinnamyl, epoxy, —CHOHCH$_2$Hal (in which Hal is a halogen atom), methylol, silyl and siloxyl groups containing one or more reactive substituents such as halogen, for example chlorine, or alkoxy, generally containing from 1 to 4 carbon atoms, for example methoxy or ethoxy, hydroxyl, amino, carboxyl, ethylenically acetylenically unsaturated crosslinkable groups, acetoacetoxy, chloroalkylsulphone, succinimido, tosylate, triflate, imidazolecarbonylamino, optionally substituted triazine, cationic and anionic groups and Y$^2$ is selected from the same group as Y$^1$.

Mixtures of functional comonomers having different groups —R$^{20}$—Q may be used. In one preferred embodiment the different monomers the groups R$^{20}$ are the same or different and each represent C$_{2-8}$-alkanediyl, and in one of the monomers the group Q is hydroxyl and in the other Q is a reactive silyl group, preferably having the formula Si (OR$^{22}$)$_3$, where each group R$^{22}$ is C$_{1-4}$-alkyl, preferably methyl or ethyl and n is 0 or 1.

For comonomers having functional groups, these may provide cross-linkability, reactivity with the polymer B or with substrates or attachment points for ligands such as pharmaceutically active agents, specific binding moieties, or antithrombogenic agents. Comonomers may alternatively include ionic groups, for instance for providing electrostatic attraction with counterionically charged moieties desired to be bonded to the coating. For instance cationic or cationisable monomers may allow loading of the zwitterionic polymer blend by anionically charged mucopolysaccharides such as heparin, which may reduce thrombogenicity of a device having surfaces formed of the solid blend still further.

In monomers of the formula I and in II and III, Y and both Y$^1$ and Y$^2$ are preferably H$_2$C=C(R)C(O)A— and H$_2$C=C (R$^5$)C(O)A$^1$—, respectively. R and R$^5$ are preferably hydrogen or, more preferably, methyl. A and A$^1$ are preferably the same and are most preferably —O—.

The ethylenically unsaturated monomers may include diluent monomers, for instance which may be added to adjust the solubility of the polymer in the coating composition from which it is coated, to adjust the hydrophilicity/phobicity, to control the flexibility of the coating, or for other reasons. Such monomers are generally non-ionic. Suitable diluent monomers are alkyl(alk)acrylates, for instance having 1 to 4 carbon atoms in the alkyl group, N-alkyl- or N,N-dialkyl(alk)acrylamides, for instance having 1 to 4 carbon atoms in the or each alkyl group, (alk)acrylamide, hydroxylalkyl(alk)acrylates, for instance having 1 to 6 carbon atoms in the alkyl group, vinyl lactams, such as vinylpyrrolidone, and styrene. Mixtures may be used.

In a particularly preferred embodiment, polymer A is a poly(2-(methacryloyloxyethyl)-2'-(trimethyl ammonium) ethyl phosphate inner salt-co-n-dodecyl methacrylate copolymer.

Preferably the zwitterionic monomer is used in the monomer mixture in a molar proportion of 5 to 50%, preferably at least 10%, preferably less than 33%, more preferably in the range 15 to 30%. The comonomer II is generally used in molar proportion of at least 50%, preferably at least 67%, more preferably in the range 70 to 85%. Where functional comonomers provide cross-linkability, the level of reactive cross-linkable groups is preferably in the range 0.1 to 25%. Diluent is preferably included in an amount up to 40%, for instance up to 25%.

Preparation of Polymer (A)

The polymers (A) bearing pendant zwitterionic groups formed from polymerisable ethylenically unsaturated groups may be prepared by conventional radical polymerisation techniques, typically using thermal, photochemical or redox initiation. Where functional comonomers capable of producing crosslinking are present, the polymerisation conditions are set such that crosslinking does not occur during polymerisation. Thus, for example, actinic radiation would not be used to prepare a polymer containing a monomer which can form crosslinks by exposure to actinic radiation.

For thermal polymerisation a temperature from 40 to 100° C., typically 50 to 80° C. is used. For photochemical polymerisation actinic radiation such as gamma, U.V., visible, or microwave radiation may be used. Typically U.V. radiation of wavelength 200 to 400 nm is used.

The polymerisation is generally performed in a liquid reaction medium, which is for instance a solution or dispersion using a non-polymerisable solvent in which the monomers and preferably also the polymer is soluble, for example acetonitrile, dimethyl formamide, chloroform, dichloromethane, ethyl acetate, dimethyl sulphoxide, dioxan, benzene, toluene, tetrahydrofuran, or where the polymer does not contain groups which react with protic solvents, water or an alkanol containing from 1 to 4 carbon atoms, e.g. methanol, ethanol or propan-2-ol. Alternatively, a mixture of any of the above solvents may be used.

The polymerisation is carried out in the presence of one or more free radical generators, usually peroxides or azo initiators, such as benzoyl peroxide, 2,2'-azo-bis(2-methylpropionitrile) or benzoin methyl ether. Other polymerisation initiators which may be used are disclosed in "Polymer Handbook", 3rd edition, Ed. J. Brandrup and E. H. Immergut, Pub. Wiley-Interscience, New York, 1989. Catalysts may be included.

Generally the polymerisation is performed for 0.1 to 72 hours, preferably 0.5 to 24 hours, and under an inert atmosphere of for example nitrogen or argon.

The polymer is generally purified by dialysis, precipitation in a non-solvent (e.g. diethyl ether or acetone) or ultrafiltration. The resulting polymer is generally dried under vacuum, eg. for 5 to 72 hours and has a molecular weight from 10,000 to 10 million, preferably from 20,000 to 1 million.

The polymerisation may be carried out under monomer starved conditions. The prime determinant of the rate of polymerisation is the rate at which the monomers are added. Thus the rate of consumption of monomers in the polymerisation vessel is substantially the same as the rate of addition of monomers to the vessel. This results in the monomer ratio remaining substantially constant throughout the monomer feed stage, at the end of which polymerisation is close to completion, for instance at least 90% complete, for instance at least 95% complete as judged by residual monomer. It is, nevertheless, preferred for polymerisation to be continued for a period after monomer feed is complete. This results in reduction of residual monomer to very low levels. The resultant polymer product can be produced with a molecular weight in the range 50,000 to 10$^6$, preferably in the range (1–5)×10$^5$ D.

The monomer starved process results in production of polymers having very low compositional variation. The zwitterionic monomers and hydrophobic comonomer having different reactivity constants, will normally polymerise at different rates. Furthermore, the monomers tend to react with growing polymer chains having end groups of the same type rather than a different type, thereby forming blocky copolymers. The polymers of the present invention tend to have a much lower compositions variation on a molecular and sub-molecular scale. Such a feature may be used to tailor polymer (A) to polymer (B) in order to provide a suitable blend according to the present invention.

The precise proportion and nature of the various comonomer used to prepare a copolymer comprising residues of a comonomer containing a zwitterionic group and a further comonomer may be adjusted to provide a copolymer which is particularly suitable for blending to a particular polymer (B), in particular to provide a particular copolymer suitable for producing a specific micro-phase segregated structure.

In addition the monomer or comonomer composition may comprise further components such as a polymerisation initiator, chain transfer agent, acid, base, surfactant, emulsifier or catalyst of conventional type each in an amount from 0.1% to 5%, typically from 0.2% to 3% and preferably about 0.5%, by weight each relative to the total weight of the monomers.

(B) Polymers Having Desirable Physical and/or Mechanical Properties

Preferably, the polymer B is a hydrophobic addition polymer, selected from polymers of alkyl(alk)acrylates most preferably straight or branched $C_{4-18}$-alkyl(meth)acrylate, more preferably a homopolymer, such as of n-dodecyl methacrylate.

Blending

Generally the blends of the present invention will contain from 1 to 90% by weight of polymer (A) containing pendant zwitterionic groups and from 99 to 10% of hydrophobic polymer (B). The precise proportions of the polymers (A) and (B) will depend upon the compatibility of the two polymers for blending and, it may be necessary to test the polymers together for their compatibility. This may be achieved by blending different proportions of the polymers (A) and (B) to obtain a blend with the desired balance of mechanical and physical properties as well as biocompatibility. In particular, the proportions of the two polymers may be adjusted so as to obtain desired impact resistance, tensile strength, flexural modulus, low temperature brittleness, friction co-efficient, film permeability, film tear resistance, film shrinkage, surface and volume resistivity, surface wettability and/or contact angle. Most particularly, the proportions are adjusted to obtain a blend which produces a micro-phase segregated structure upon removal of a solvent from the blend solution or dispersion.

The applicants have found that a zwitterion group-containing copolymer prepared by copolymerization with a comonomer, as hereinbefore described, can give a stable uniform solution when dissolved together with a hydrophobic polymer B, in a single solvent or mixed solvent. Such novel liquid blends form part of the invention. Evaporation of the solvent results in phase separation and the production of micro-phase segregated structure at the surface of an formed or coated article. Domains of several hundred micrometers to as little as a few nanometers can be formed, comprising the zwitterion containing copolymer, the domains being uniformly distributed at the surface of the hydrophobic polymer.

Preferred solvents for forming the liquid blend of the invention include but are not restricted to low boiling point (<100° C.) chlorinated solvents. For example, dichlororethane or chloroform. Chloroform is particularly preferred. Other solvents include lower alcohols such as methanol, ethanol, n-propanol, propane-2-ol and solvents such as esters and ethers, paricularly ethylacetate and tetrahydrofuran.

The minimum quantity of polymer (A) will depend upon the particular polymer (B), the content of zwitterionic groups in the polymer (A) and the desired use of the blend. Preferably the blend will contain at least 1%, more preferably 10% and still more preferably 30% of polymer (A).

In a process of the invention the liquid blend is used to coat or form an article, for instance by shaping the liquid and then removing the solvent by evaporation. In a preferred embodiment a coating of the liquid blend is formed on the surface of a preformed article and the solvent is removed by evaporation to form a coating of solid blend A and B. The polymers of the blend may, after coating, be bound to the article by hydrogen-bonding interactions, by chemical reaction to provide a covalent bond with the underlying polymer surface or by counterionic attraction between oppositely charged ionic groups on the zwitterionic polymer and on the coated surface. Particularly preferred surfaces to be coated include silicones, polyurethanes, polyalkacrylates, polystryene, polycarbonate, and metals (particularly stainless steel).

The hydrophobic domains of the novel solid blend may also be expressed at the surface of a coated article produced by the process of the invention. The overall concept is based on the use of the zwitterionic group expression at the article surface to reduce non-specific adsorption of proteins and other biological moieties, whilst the hydrophobic domains provide controlled sites of hydrophobicity that may provide anchorage for cells or other proteinceous deposits to spread, grow or accumulate at these sites. The microdomains are for instance less than 1 $\mu$m in diameter, usually less than about 500 $\mu$m, often less than 200 $\mu$m in diameter.

Alternatively, the hydrophobic domains may be destabilized and removed to provide selective exposure of the underlying article surface which may provide anchorage for biological moieties as described above. Such destabilization can be effected in a number of ways, for example, contact with water or other solvents, aqueous or organic may disrupt the hydrophobic domains. It is believed that polymer B resiles from the surface into the bulk of the coating and polymer A is relatively more exposed upon such contact.

The utility of this invention is primarily in the medical field, for instance for any instrument which requires partial assimilation with biological systems. Such instruments are for instance contact lenses, corneal grafts, vascular grafts, intraocular lenses and other surgical implants or prostheses and bioseparation apparatus, tubing for use in prostheses, in extra corporeal circuitry. In particular, they are suitable for use as contact lenses, corneal grafts, intra-ocular lenses and other ophthalmic implants.

In addition, the blends of the present invention may further comprise conventional additives used in polymeric materials such as plasticisers, fillers, colourants, UV absorbers, anti-oxidants and/or preservatives, such as biocides, which may be included in conventional amounts so as to be compatible with the polymers present in the blend.

BRIEF DESCRIPTION OF THE DRAWINGS

FIG. 6 shows surface plasmon resonance studies of protein interaction on various blends as described in Example 3, specifically:

The present invention will now be illustrated by the following Examples:

EXAMPLE 1

Preparation for poly(2-(methacryloyloxyethyl)-2'-(trimethyl ammonium) ethyl phosphate inner salt-co-n-dodecyl methacrylate (MPC-co-DM$_6$ (1:6) blended with poly (dodecylmethacrylate) (Poly DM) matrix A 1:1 molar quantity of MPC-co-DM$_6$ and Poly DM was dissolved in chloroform to produce a 0.5% w/w solution. 130 µg of the solution was dropped onto a spinning silvered glass plate. The solvent evaporates to give a polymer coated disc.

Figure 2:
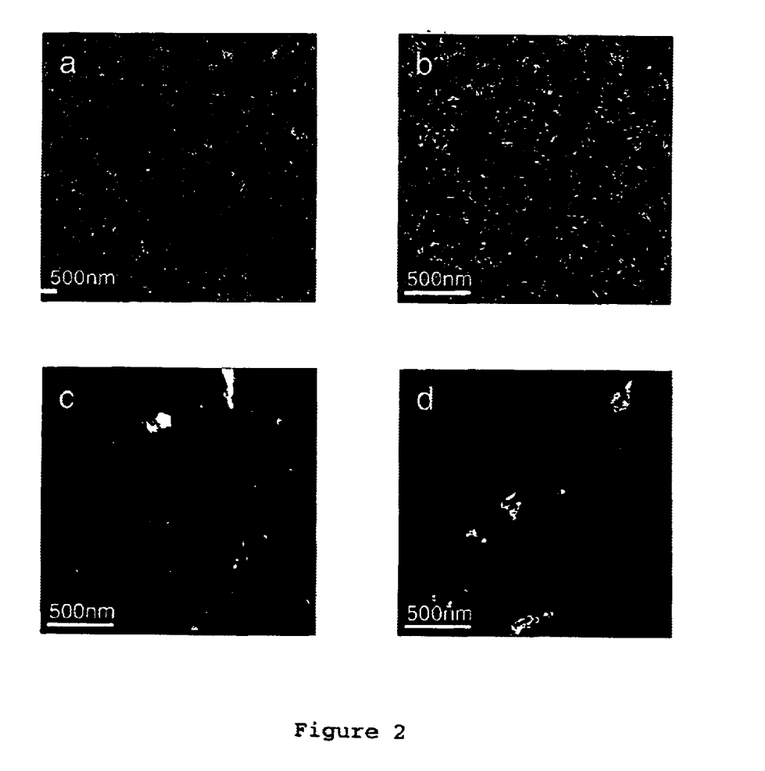
FIG. 2 shows phase segregation in MPC-LM$_6$:poly(LM) blends of effective formulae (a) MPC-LM$_{14}$ (b) MPC-LM$_{35}$ (c) MPC-LM$_{50}$ (d) MPC-LM$_{100}$ as described in Example 1.

AFM analysis with phase imaging of the individual polymers shows an homogeneous, non phase-separated surface for both. However, the same analysis of the blends of the two polymers show that the two are immiscible, surface segregation with nanometer sized domains being formed throughout the range of blends studied. In phase mode, the two different phases are represented as dark and light regions on the image. By use of amplitude-phase-distance curves, a fingerprint of both the dark and light regions can be obtained and compared with that obtained from coatings of the individual polymers. This showed unequivocally that the area represented by the dark regions was due to poly(DM) and the light regions poly(MPC-co-DM). Analogous methods were used to provide blends of MPC-co-DM$_{14}$:PolyDM, MPC-co-DM$_{35}$:PolyDM, MPC-co-DM$_{50}$:PolyDM and MPC-co-DM$_{100}$:PolyDM the results of which are shown in FIG. 2. These show phase segregation in MPC-co-DM:PolyDM blends of effective formula (a) MPC-co-DM$_{14}$, (b) MPC-co-DM$_{35}$, (c) MPC-co-DM$_{50}$ and (d) MPC-co-DM$_{100}$.

Figure 1:
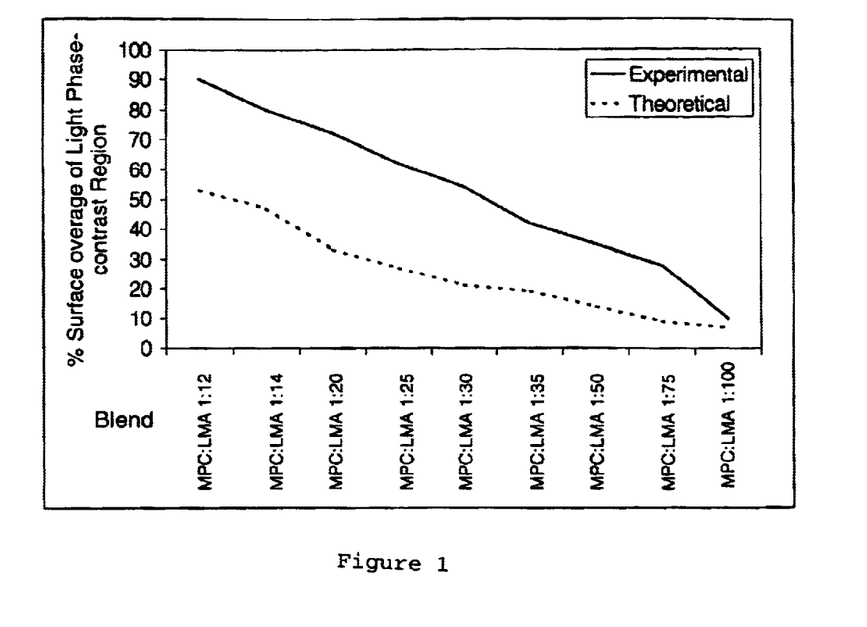
FIG. 1 shows comparison of theoretically calculated and experimentally derived surface coverage of PLMA, showing the preferential surface expression of MPC:LMA (1:6) as described in Example 1.

Bearing analysis on the images allows a calculation of the relative area covered by both light and dark regions. When these values for the various blends are plotted against that theoretically expected for a mixture of the two polymers (FIG. 1), it becomes evident that the poly(MPC-coDM$_6$) is being preferentially expressed at the surface. Hence only a small amount of poly(MPC-coDM$_6$) is needed to produce a relatively PC-enriched surface.

EXAMPLE 2

Poly(n-butyl methacrylate) (PBMA):[MPC:LMA (1:2)]

Figure 3:
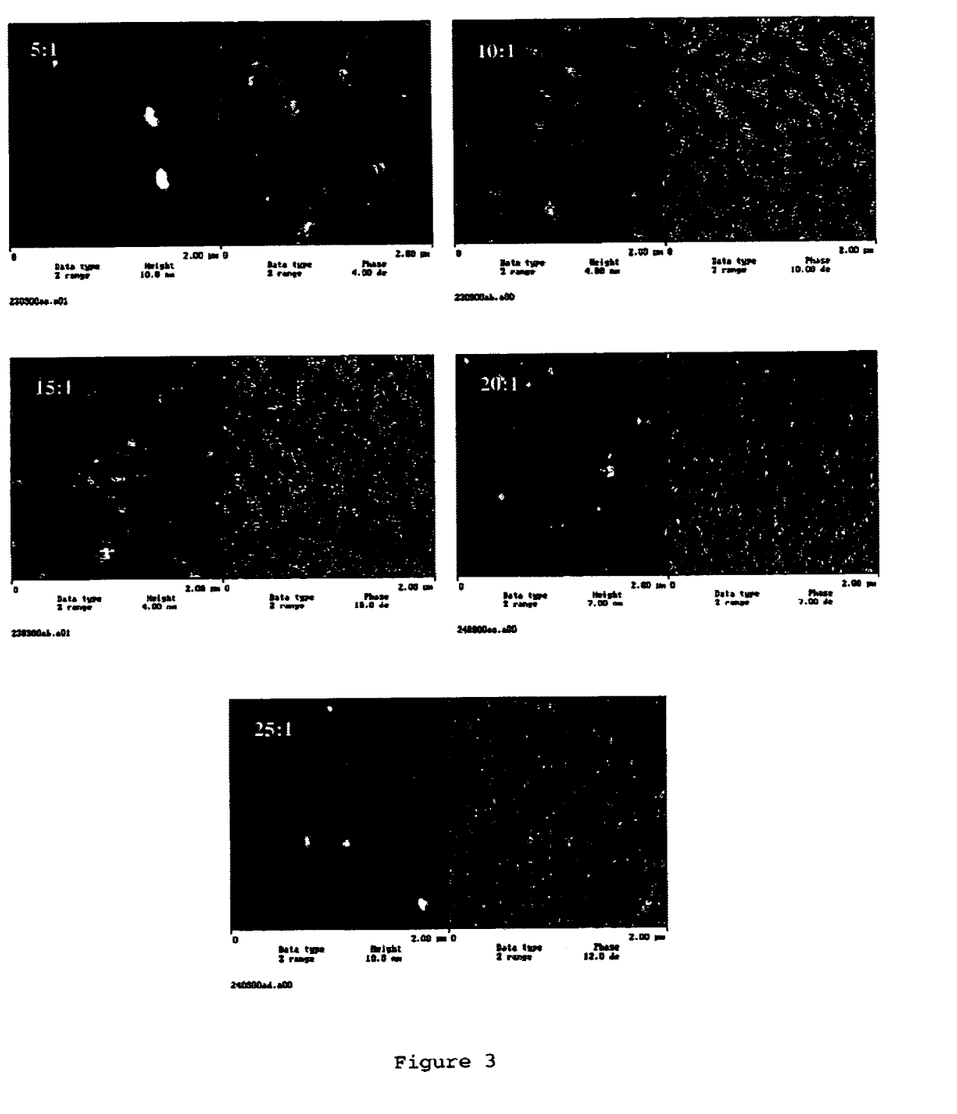
FIG. 3 shows AFM of Poly(n-butyl methacrylate): [MPC:LMA (1:2)] Blends as described in Example 2.

If coatings from blends of poly(n-butyl methacrylate) (PBMA) with MPC:LMA (1:2) are made and imaged as described in Example 1, similar surface morphologies are observed. FIG. 3 shows a series of AFM topography and phase images for blends of PBMA:[MPC:LMA (1:2)]. In this case, the dark region represents MPC:LMA (1:2), as its presence on the surface can be clearly seen to decrease as the amount of PBMA in the blend increases.

COMPARATIVE EXAMPLE 1

Poly(methyl methacrylate) (PBMA):[MPC:LMA (1:2)]

Figure 4:
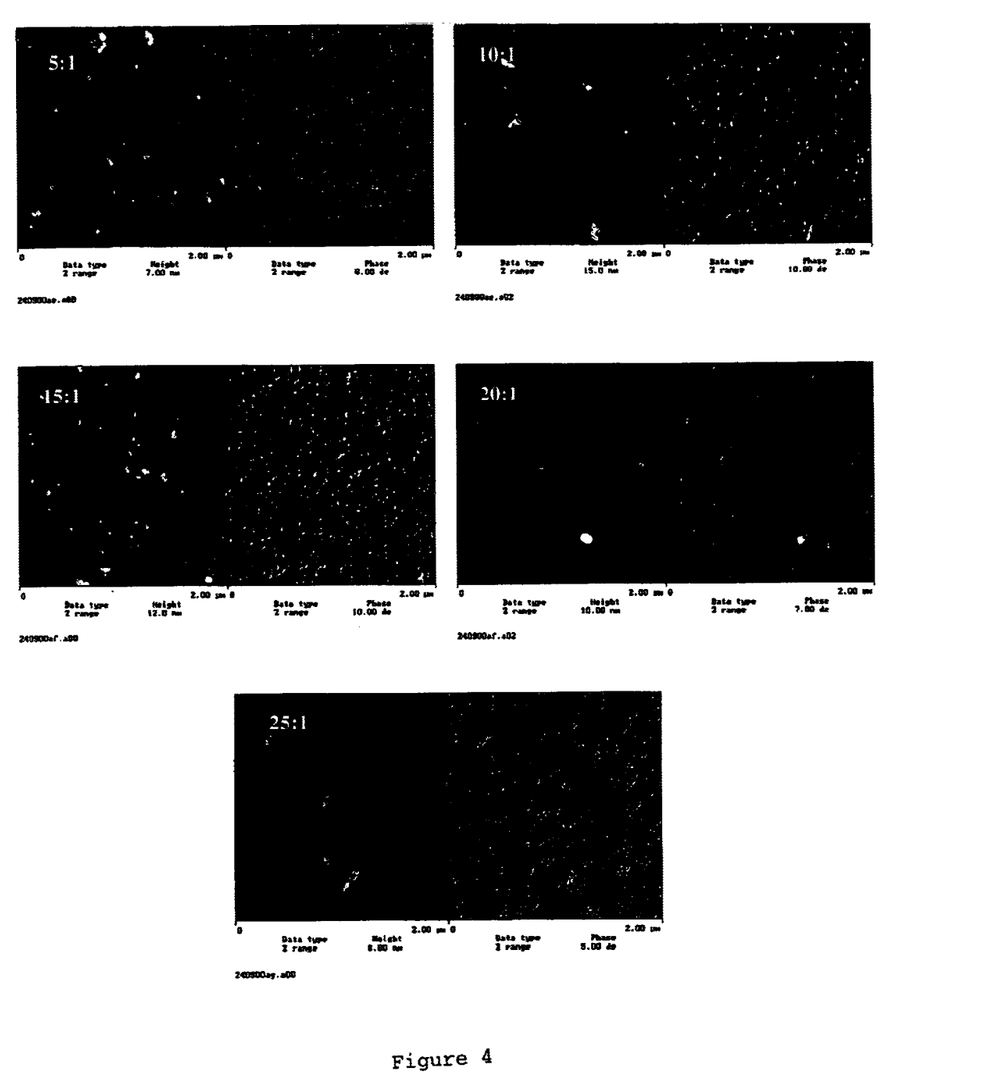
FIG. 4 shows AFM of Poly(methyl methacrylate): [MPC:LMA (1:2)] Blends as described in comparative Example 1.

If coatings from blends of poly(methyl methacrylate) (PMMA) with MPC:LMA (1:2) are made and imaged as described in Example 1, no phase separation can be detected for any of the blends (FIG. 4). It is well known that in blend systems, micelles of one polymer can be formed that are able to migrate to interfaces. The energetics that drive the micellisation will be dependent upon the chemical structure of the two polymers being blended together. In Examples 1 and 2, a PC-copolymer that has a long alkyl chain component is being blended with another alkyl methacrylate. In the case of methyl methacrylate, it may be that this shortest of the alkyl chain methacrylates does not promote the micelle formation and hence no preferential surface expression of the copolymer. Instead, an homogeneous mixture of the two polymers results.

REFERENCE EXAMPLE 1

Surface Plasmon Resonance Investigations of Blend Surfaces

Figure 5:
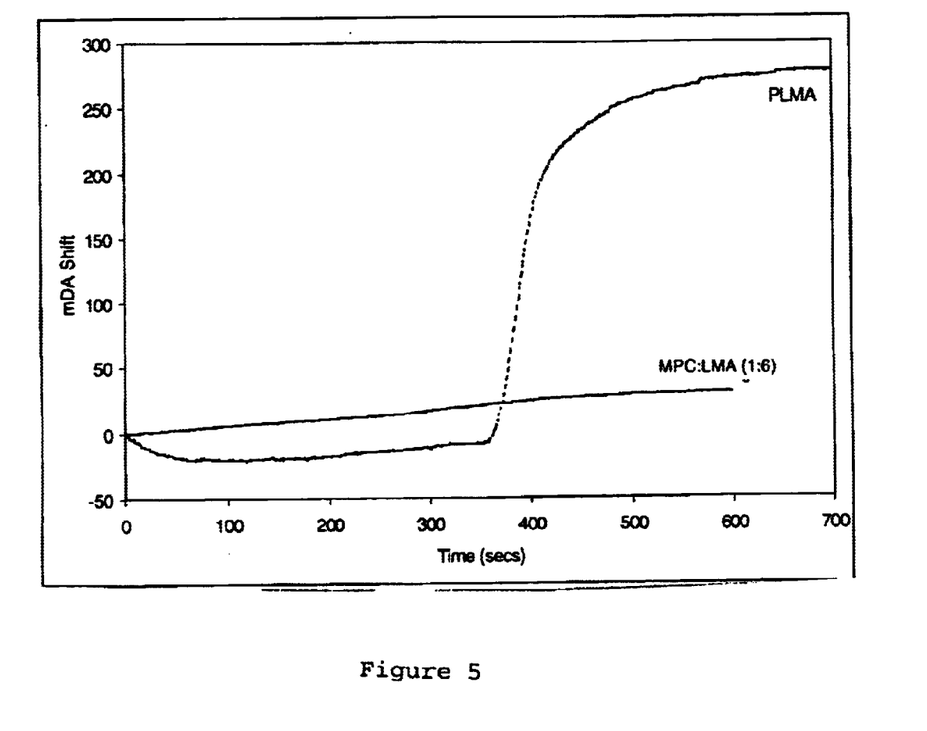
FIG. 5 shows SPR Traces of fibrinogen passing over PLMA and MPC:LMA (1:6), demonstrating the protein-resistant nature of MPC:LMA (1:6) and the non-biocompatibility of PLMA as described in Example 3.

Surface plasmon resonance (SPR) is a technique that can determine in-situ the amount of protein interacting with a surface. FIG. 5 shows the SPR traces for the plasma protein fibrinogen (0.05 mg/ml) when passed over PLMA and MPC:LMA (1:6). In SPR, protein adsorption is accompanied by an increase in the angle of minimum light reflection (termed $\theta_{SPR}$). Passing fibrinogen over the PLMA coating caused an increase in $\theta_{SPR}$ of 286±9 mDA, whilst the coating of MPC:LMA (1:6) no increase was detected. PLMA is a very hydrophobic polymer due to the $C_{12}H_{25}$ sidechain and the long hydrocarbon backbone. In contrast, MPC:LMA (1:6 is hydrophilic due to the PC headgroup which has been shown to have a strong affinity for water as a result of its zwitterionic structure. It has been hypothesised that the hydrophilicity of a materials surface has a major influence on the amount of protein that will adsorb and hence can explain the behaviour of these two polymers.

EXAMPLE 3

Figure 6A:
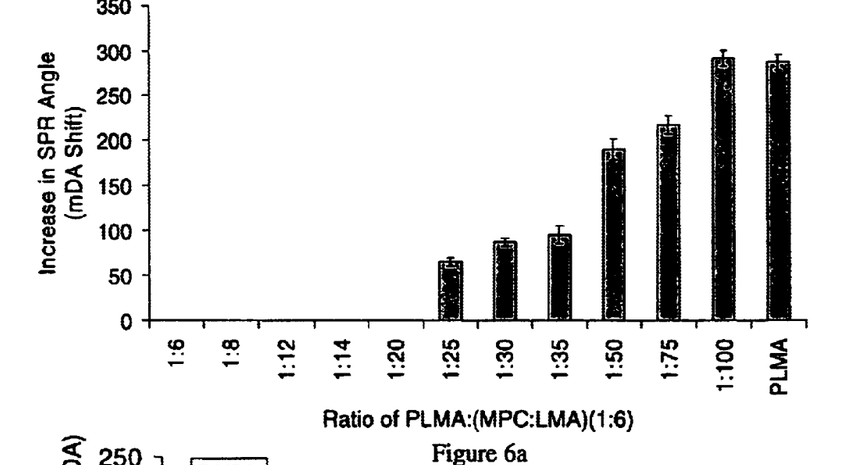
FIG. 6a shows a comparison of the increase in $\theta_{SPR}$ for different composition PLMA:[MPC:LMA (1:6)] blends exposed to fibrinogen.
Figure 6B:
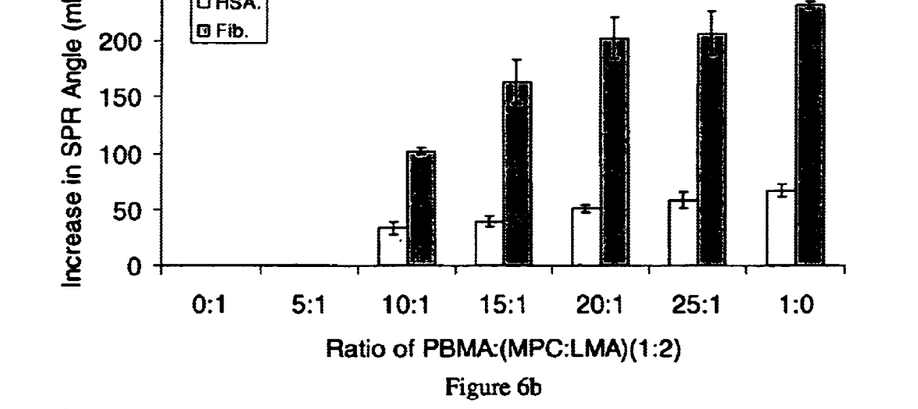
FIG. 6b shows a comparison of the increase in $\theta_{SPR}$ for different composition PBMA:[MPC:LMA (1:2)] blends exposed to human serum albumin (HAS) and fibrinogen (Fib).
Figure 6C:
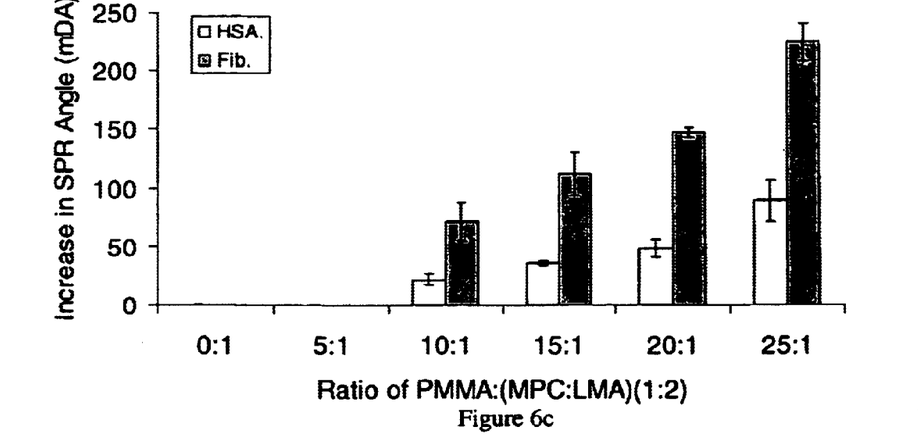
FIG. 6c shows a comparison of the increase in $\theta_{SPR}$ for different composition PMMA:[MPC:LMA (1:2)] blends exposed to human serum albumin (HAS) and fibrinogen (Fib).

FIG. 6 shows the SPR traces for protein adsorption to a variety of blends: (a) PLMA:[MPC:LMA (1:6)]; (b) PBMA: [MPC:LMA (1:2)]; (c) PMMA:[MPC:LMA (1:2)]. These traces demonstrate that for ratios below 2.7:1 for PLMA: [MPC:LMA (1:6)] invention and 5:1 for PBMA: [MPC:LMA (1:2)] (invention) & PMMA:[MPC:LMA (1:2) (comparative), protein does not adsorb to the coating surface. Obviously, more matrix polymer can be tolerated in the blend system based on MPC:LMA (1:2) in which there is more MPC compared to the MPC:LMA (1:6) system. The amount of protein adsorbing in each case is clearly dependent upon the ratio of the blend and ultimately the amounted of PC expressed at the surface.

What is claimed is:

1. A polymer blend at the surface of an article for use in a biomedical application comprising:

(A) a polymer A, bearing zwitterionic pendant groups; and formed from a mixture of ethylenically unsaturated monomers comprising i) 5 to 70 mole % of a monomer containing a zwitterionic group, of the formula

YBX          I wherein

B is a straight or branched alkylene (alkanediyl), alkyleneoxaalkylene or alkylene oligo-oxaalkylene chain optionally containing one or more fluorine atoms up to and including perfluorinated chains or, if X or Y contains a terminal carbon atom bonded to B, a valence bond;

X is a zwitterionic group; and

Y is an ethylenically unsaturated polymerisable group selected from $CH_2$=C(R)—$CH_2$—O—, $CH_2$=C(R)—$CH_2$OC(O)—, $CH_2$=C(R)OC(O)—, $CH_2$=C(R)—O—, $CH_2$=C(R)$CH_2$OC(O)N($R^1$)—, $R^2$OOCCR=CRC(O)—O—, RCH=CHC(O)O—, RCH=C(COO$R^2$)$CH_2$—C(O)—O—, and wherein:

R is hydrogen or a $C_1$-$C_4$ alkyl group;

$R^1$ is hydrogen or a $C_1$-$C_4$ alkyl group or $R^1$ is —B—X where B and X are as defined above; and $R^2$ is hydrogen or a $C_{1-4}$ alkyl group;

A is —O— or —$NR^1$—;

K is a group —$(CH_2)_p$OC(O)—, —$(CH_2)_p$C(O)O—, —$(CH_2)_p$OC(O)O—, —$(CH_2)_p$$NR^5$—, —$(CH_2)_p$$NR^3$C(O)—, —$(CH_2)_p$C(O)$NR^3$—, —$(CH_2)_p$$NR^3$C(O)O—, —$(CH_2)_p$OC(O)$NR^3$—, —$(CH_2)_p$$NR^3$C(O)$NR^3$— (in which the groups $R^3$ are the same or different), —$(CH_2)_p$O—, —$(CH_2)_p$$SO_3$—, or, optionally in combination with B, a valence bond p is from 1 to 12; and $R^3$ is hydrogen or a $C_1$-$C_4$ alkyl group; and ii) 50 to 95 mol % of a monomer having the general formula II $Y^1R^4$          II wherein $Y^1$ is selected from $CH_2$=C($R^5$)—$CH_2$—O—, $CH_2$=C($R^5$)—$CH_2$OC(O)—, $CH_2$=C($R^5$)OC(O)—, $CH_2$=C($R^5$)—O—, $CH_2$=C($R^5$)$CH_2$OC(O)N($R^5$)—, $R^7$OOCC$R^5$=C$R^5$C(O)—O—, $R^5$CH=CHC(O)O—, $R^5$CH=C(COO$R^7$)$CH_2$—C(O)—O—, and wherein:

$R^5$ is hydrogen or a $C_1$-$C_4$ alkyl group;

$R^6$ is hydrogen or a $C_1$-$C_4$ alkyl group or $R^6$ is $R^4$;

$R^7$ is hydrogen or a $C_{1-4}$ alkyl group;

$A^1$ is —O— or —$NR^6$—; and $K^1$ is a group —$(CH_2)_q$OC(O)—, —$(CH_2)_q$C(O)O—, —$(CH_2)_q$OC(O)O—, —$(CH_2)_q$$NR^8$—, —$(CH_2)_q$$NR^8$C(O)—, —$(CH_2)_q$C(O)$NR^8$—, —$(CH_2)_q$$NR^8$C(O)O—, —$(CH_2)_q$OC(O)$NR^8$—, —$(CH_2)_q$$NR^8$C(O)$NR^8$— (in which the groups $R^8$ are the same or different), —$(CH_2)_q$O—, —$(CH_2)_q$$SO_3$—, or a valence bond q is from 1 to 12;

and $R^8$ is hydrogen or a $C_1$-$C_4$ alkyl group;

and $R^4$ is selected from the group consisting of a straight, branched and cyclic $C_{6-24}$ alkyl, alkoxyalkyl having a total of 6 to 24 carbon atoms or oligoalkoxyalkyl chain $C_pH_{2p+1}(OC_qH_{2q})_s$ in which p is 3–24, s is in the range 2 to 50, in the groups $C_qH_{2q}$ the q's are the same or different, each q is 2–6 provided that at least half of the q's are 3 or more when p is less than 8, $C_{1-24}$ fluoroalkyl, $C_{6-24}$ alkenyl, $C_{6-24}$ alkynyl, $C_{6-24}$ aryl, $C_{9-24}$ aralkyl and siloxane groups —$(CR^{18a}_2)_{qq}$ $(SiR^{19}_2)(OSiR^{19}_2)_{pp}R^{19}$ in which each group $R^{18}$ is the same or different and is hydrogen or alkyl of 1 to 4 carbon atoms, or aralkyl, each group $R^{19}$ is alkyl of 1 to 4 carbon atoms, qq is from 1 to 6 and pp is from 0 to 49,

(B) a hydrophobic addition polymer B, selected from the group consisting of silyl(alk)acrylates, $C_{4-24}$ alkyl(alk)acrylamides, di($C_{4-24}$)alkyl(alk)acrylamides, and $C_{4-24}$ alkyl (alk)acrylate polymers, wherein the structure of the blend exhibits phase separation forming a microphase segregated structure at said surface.

2. A blend according to claim 1 in which the zwitterionic group has the general formula III

III in which the moieties $A^2$ and $A^3$, which are the same or different, are —O—, —S—, —NH— or a valence bond, preferably —O—, and $W^+$ is a group comprising an ammonium, phosphonium or sulphonium cationic group and a group linking the anionic and cationic moieties which is preferably a $C_{1-12}$-alkanediyl group, preferably in which $W^+$ is a group of formula

$W^1$ is alkanediyl of 1 or more, preferably 2–6 carbon atoms optionally containing one or more ethylenically unsaturated double or triple bonds, disubstituted-aryl (arylene), alkylene arylene, arylene alkylene, or alkylene aryl alkylene, cycloalkanediyl, alkylene cycloalkyl, cycloalkyl alkylene or alkylene cycloalkyl alkylene, which group $W^1$ optionally contains one or more fluorine substituents and/or one or more functional groups; and either the groups $R^9$ are the same or different and each is hydrogen or alkyl of 1 to 4 carbon atoms, preferably methyl, or aryl, such as phenyl, or two of the groups $R^9$ together with the nitrogen atom to which they are attached form an aliphatic heterocyclic ring containing from 5 to 7 atoms, or the three groups $R^9$ together with the nitrogen atom to which they are attached form a fused ring structure containing from 5 to 7 atoms in each ring, and optionally one or more of the groups $R^9$ is substituted by a hydrophilic functional group, and the groups $R^{10}$ are the same or different and each is $R^9$ or a group $OR^9$, where $R^9$ is as defined above; or Het is an aromatic nitrogen-, phosphorus- or sulphur-, preferably nitrogen-, containing ring, for example pyridine.

3. A blend according to claim 2 in which the zwitterionic group of formula III, has the general formula IV:

IV where the groups $R^{11}$ are the same or different and each is hydrogen or $C_{1-4}$ alkyl, and m is from 1 to 4, in which preferably the groups $R^{11}$ are the same preferably methyl.

4. A blend according to claim 1 in which group $R^4$ is a $C_8$-$C_{16}$ alkyl, alkenyl or alkynyl group, preferably a $C_8$-$C_{16}$ alkyl, most preferably a $C_{12}$ alkyl group.

5. A blend according to claim 1 in which the zwittenonic monomer is used in the monomer mixture in a molar proportion of at least 10%, preferably in the range of 15 to 30%.

6. A blend according to claim 1 in which polymer A is a poly(2-(methacryloyloxyethy-2'-(trimethyl ammonium) ethyl phosphate inner salt-co-n-dodecyl methacrylate copolymer.

7. A blend according to claim 1 in which polymer B is a homopolymer of a $C_{4-18}$ alkylmethacrylate, preferably dodecylmethacrylate.

8. A blend according to claim 1 which contains 1 to 90% (by weight) of polymer A and 10 to 99% of polymer B, preferably at least 10% of polymer A.

9. A process for producing a coating of a blend as defined in claim 1 comprising the steps of:
   a) dissolving or dispersing polymer A and polymer B in a solvent to form a liquid blend;
   b) applying the liquid blend to an article or surface to form a coating of liquid thereon;
   c) substantially removing the solvent from the coating whereby a solid blend having a micro-phase segregated surface structure is formed.

10. A process according to claim 9 in which the solvent is a chlorinated solvent, preferably chloroform.

11. A composition comprising a blend of polydodecylmethacrylate and poly(2-(methacryloyloxyethyl)-2'-(trimethyl ammonium) ethyl phosphate inner salt-co-n-dodecyl methacrylate copolymer.

12. A composition according to claim 11 in which the ratio of polydodecylmethacrylate and poly(2-(methacryloyloxyethyl)-2'-(trimethyl ammonium) ethyl phosphate inner salt-co-n-dodecyl methacrylate copolymer is in the range 1:1 to 50:1.

13. A composition according to claim 11 which is a liquid blend comprising at least one solvent.

* * * * *